(12) United States Patent
Singh et al.

(10) Patent No.: US 12,121,381 B2
(45) Date of Patent: Oct. 22, 2024

(54) GENERATING X-RAY IMAGES AND INDICATING DIAGNOSES ASSOCIATED WITH THE X-RAY IMAGES

(71) Applicant: Micron Technology, Inc., Boise, ID (US)

(72) Inventors: Yashvi Singh, Boise, ID (US); Tanya Khatri, Boise, ID (US); Fatma Arzum Simsek-Ege, Boise, ID (US); Yanni Wang, Meridian, ID (US)

(73) Assignee: Micron Technology, Inc., Boise, ID (US)

( * ) Notice: Subject to any disclaimer, the term of this patent is extended or adjusted under 35 U.S.C. 154(b) by 263 days.

(21) Appl. No.: 17/652,910

(22) Filed: Feb. 28, 2022

(65) Prior Publication Data

US 2023/0200762 A1    Jun. 29, 2023

Related U.S. Application Data

(60) Provisional application No. 63/266,137, filed on Dec. 29, 2021.

(51) Int. Cl.
*A61B 6/00* (2024.01)
*A61B 6/46* (2024.01)

(52) U.S. Cl.
CPC .......... *A61B 6/4405* (2013.01); *A61B 6/4411* (2013.01); *A61B 6/463* (2013.01); *A61B 6/5205* (2013.01); *A61B 6/5217* (2013.01); *A61B 6/547* (2013.01); *A61B 6/563* (2013.01)

(58) Field of Classification Search
None
See application file for complete search history.

(56) References Cited

U.S. PATENT DOCUMENTS

| | | | |
|---|---|---|---|
| 2012/0039432 A1* | 2/2012 | Kondo | A61B 6/545 378/4 |
| 2013/0184537 A1* | 7/2013 | Konuma | A61B 6/586 600/300 |
| 2013/0343526 A1* | 12/2013 | Putterman | H01J 35/02 378/121 |
| 2015/0347686 A1* | 12/2015 | Ortiz | G16H 10/60 705/3 |
| 2017/0027532 A1* | 2/2017 | Joshi | A61B 6/40 |
| 2017/0055925 A1* | 3/2017 | Lee | A61B 6/465 |
| 2019/0350546 A1* | 11/2019 | He | A61B 6/42 |

\* cited by examiner

*Primary Examiner* — Hoon K Song
(74) *Attorney, Agent, or Firm* — Harrity & Harrity, LLP

(57) ABSTRACT

In some implementations, a device may produce, via an x-ray module, x-rays to be directed towards a body part. The device may detect, via a sensor, the x-rays reflected from the body part. The device may generate, via the sensor, signals based on the x-rays reflected from the body part. The device may generate, via a processor, an x-ray image of the body part based on the first signals. The device may transmit the x-ray image to a server. The device may receive, from the server, a message that indicates a diagnosis associated with the x-ray image. The device may display, via a user interface, the x-ray image and information associated with the diagnosis associated with the x-ray image.

25 Claims, 11 Drawing Sheets

GENERATING X-RAY IMAGES AND INDICATING DIAGNOSES ASSOCIATED WITH THE X-RAY IMAGES

CROSS-REFERENCE TO RELATED APPLICATION

This Patent Application claims priority to U.S. Provisional Patent Application No. 63/266,137, filed on Dec. 29, 2021, and entitled "GENERATING X-RAY IMAGES AND INDICATING DIAGNOSES ASSOCIATED WITH THE X-RAY IMAGES." The disclosure of the prior Application is considered part of and is incorporated by reference into this Patent Application.

TECHNICAL FIELD

The present disclosure generally relates to x-ray imaging and, for example, generating x-ray images and indicating diagnoses associated with the x-ray images.

BACKGROUND

X-ray is a penetrating form of high-energy electromagnetic radiation. X-rays may have a wavelength ranging from 10 picometers to 10 nanometers, corresponding to frequencies in the range of 30 petahertz to 30 exahertz and energies in the range of 124 electron volts (eV) to 124 keV. X-rays may be used for medical imaging by a healthcare provider. X-rays may be absorbed at different rates by different parts of the body, and a detector may detect the X-rays after passing through the body and generate an image based on the X-rays that have passed through the body. A machine that emits X-rays may be used to examine bones, joints, or internal organs of humans and other animals. X-rays may be used to detect problems, such as bone fractures and breaks, tooth problems, spine problems, non-cancerous and cancerous bone tumors, lung problems, heart problems, and cancers.

DETAILED DESCRIPTION

Figure 1A:
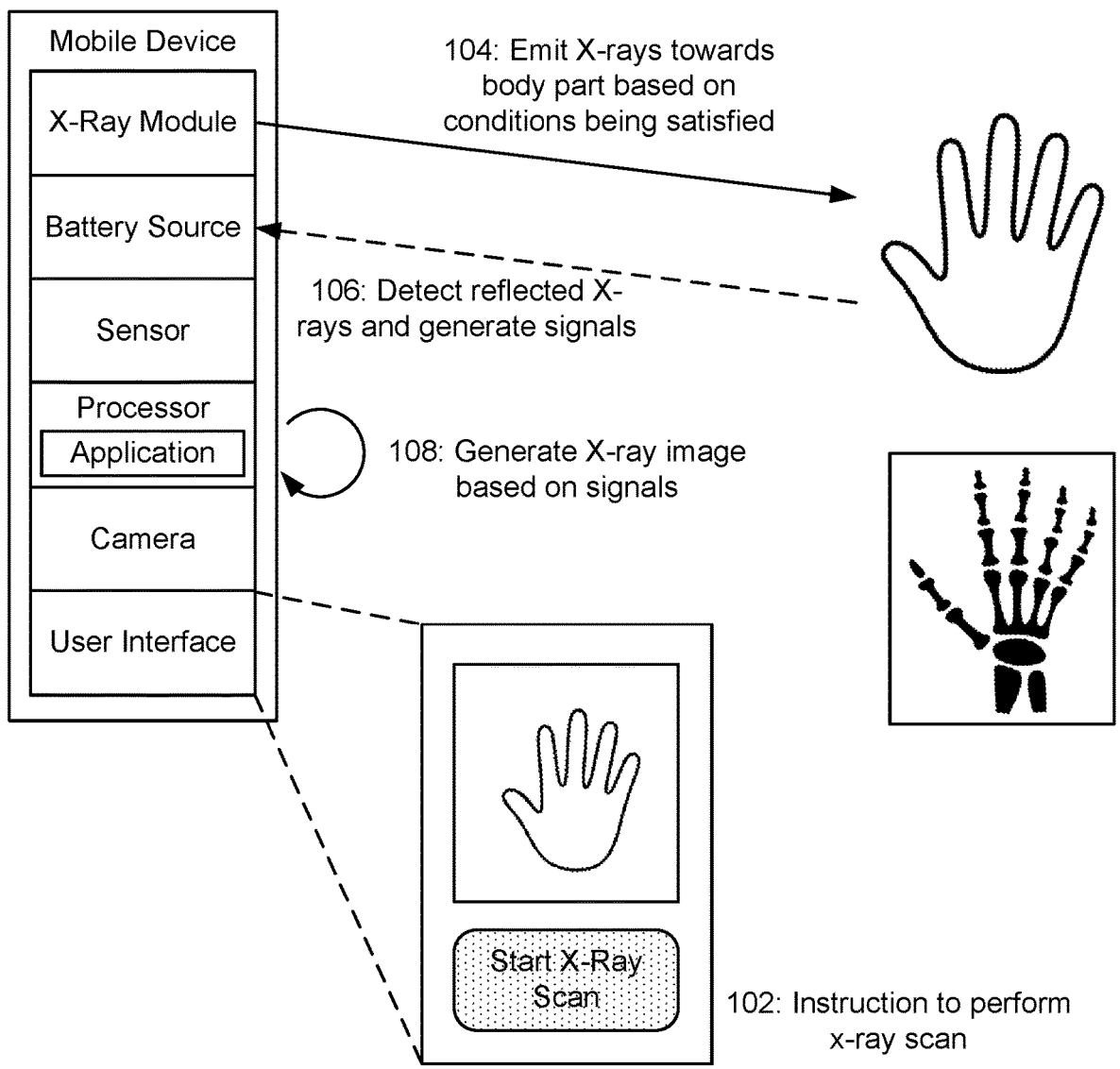
FIGS. 1A-1C are diagrams of an example relating to generating x-ray images and indicating diagnoses associated with the x-ray images.

X-ray is a penetrating form of high-energy electromagnetic radiation, which may be used for medical imaging. A machine may emit X-rays at a body part to be imaged. The X-rays may be absorbed at the body part. A detector may detect the X-rays after passing through the body part. An X-ray image may be formed based on the X-rays that pass through the body part. Dense areas of the body part, such as bone, may be harder for the X-rays to pass through and may show up as clear white areas on the X-ray image. Soft areas with more tissue, such as a heart or lung, may be easier for the X-rays to pass through and may show up as darker areas on the X-ray images. A healthcare provider may be able to determine various problems (e.g., bone fracture, cancer, and so on) based on the X-ray image.

One problem is that, after an injury occurs to a body part of a person, the person may need to travel to a hospital to have the injury examined by a first healthcare provider (e.g., an emergency room physician). The person may need to make an appointment and/or wait at the hospital until the first healthcare provider is available to visit with the person. The person may need to wait until an X-ray room is available and until a second healthcare provider (e.g., a radiologist) is available to perform the X-ray of the body part. After an X-ray image is produced of the body part, results of the X-ray may be conveyed by the first healthcare provider and/or the second healthcare provider. This process may take an inordinate amount of time and may involve numerous steps before the X-ray image and corresponding diagnosis is available to the person. Further, the person suffering from the injury may suffer prolonged pain and discomfort during the amount of time needed to visit the hospital and obtain the X-ray image. In some cases, the injury may be apparent to the person (e.g., a broken finger), but the person may still need to go through the process to obtain the X-ray image.

Depending on the results of the X-ray, additional treatment may be needed to treat the injury (e.g., a cast for a broken bone), which may be convenient when the person is already at the hospital. However, when additional treatment is not needed or common medication is prescribed, the person may have spent a relatively large amount of time during the process.

In some cases, the X-ray may not be for an injury, but rather may be associated with a periodic or routine exam (e.g., a routine chest scan to check for cancer). The person may travel to the hospital to have the X-ray performed, and then may meet with a healthcare provider during the same visit or at a subsequent visit to discuss the results of the X-ray. Again, multiple trips may be needed for the person to travel to the hospital in order to have the X-ray performed, which may be inconvenient for the person.

Another problem is that, in some cases, the X-ray image may be examined by an inexperienced healthcare provider, and additional consultation with more experienced healthcare providers may be needed before a diagnosis is available to the person, which may further delay the process. Thus, an accuracy of the diagnosis may be affected depending on an experience level of the healthcare provider. The accuracy of diagnosing X-rays may not be consistent across healthcare providers and across different body parts that are being X-rayed.

In some implementations described herein, to solve the problems described above, as well as how to generate x-ray images and indicate diagnoses associated with the x-ray images, a technical solution is described herein for generating, at a mobile device, an x-ray image of a body part and determining a diagnosis associated with the x-ray image. The mobile device may produce, via an x-ray module of the mobile device, x-rays to be directed towards the body part. The mobile device may detect, via a first sensor of the mobile device, the x-rays reflected from the body part. The mobile device may generate, via the first sensor, first signals based on the x-rays reflected from the body part. The mobile device may generate, via a processor of the mobile device, the x-ray image of the body part based on the first signals. The mobile device may determine the diagnosis associated with the x-ray image. For example, the mobile device may transmit, via a transceiver of the mobile device, the x-ray image to a server. The mobile device may receive, via the transceiver and from the server, a first message that indicates the diagnosis associated with the x-ray image. The diagnosis may be based on a comparison of the x-ray image of the body part to a plurality of x-ray images stored at the server. The mobile device may display, via a user interface of the mobile device, the x-ray image and information associated with the diagnosis associated with the x-ray image. The mobile device may transmit, to a system associated with a healthcare provider, the x-ray image and the first message that indicates the diagnosis associated with the x-ray image.

As a result, a user may scan their own body part using the mobile device, or another user may scan the body part using the mobile device on behalf of the user. The user may be notified of the diagnosis associated with the body part in a relatively short period of time. The user may not need to travel to a hospital in order to obtain the x-ray image. Rather, the user may be notified of the diagnosis and a confidence score associated with the diagnosis. At this point, the user may determine whether to travel to the hospital for additional treatment, which may prevent unnecessary trips to the hospital. The x-ray image and the diagnosis may be automatically transmitted to the healthcare provider, so if the user does visit the hospital, the x-ray image and the diagnosis may already be available to the healthcare provider. The healthcare provider may use the diagnosis as supplementary information when performing their own diagnosis. An ability for the user to scan their own body part using the mobile device and obtain the x-ray image may streamline and simplify an x-ray imaging process, which may reduce time spent and resources for both the user and the healthcare provider.

Further, since the x-ray image may be compared with the plurality of x-ray images, for example, using a machine learning model, artificial intelligence model, or other related techniques, an accuracy of the diagnosis may be consistent with or better than a diagnosis offered by a healthcare provider, especially when the healthcare provider is less experienced. The machine learning model may be formed using the plurality of x-ray images, which may include x-ray images from a plurality of patients, where each x-ray image may be associated with a confirmed diagnosis (or a truth). The machine learning model may continually be trained using additional x-ray images, thereby continually improving accuracy when determining diagnoses associated with the x-ray images. Thus, an ability for the mobile device to obtain x-ray images, and an ability for the x-ray images to be analyzed using the machine learning model, may improve an accuracy when diagnosing injuries from the x-ray images.

Figure 1B:
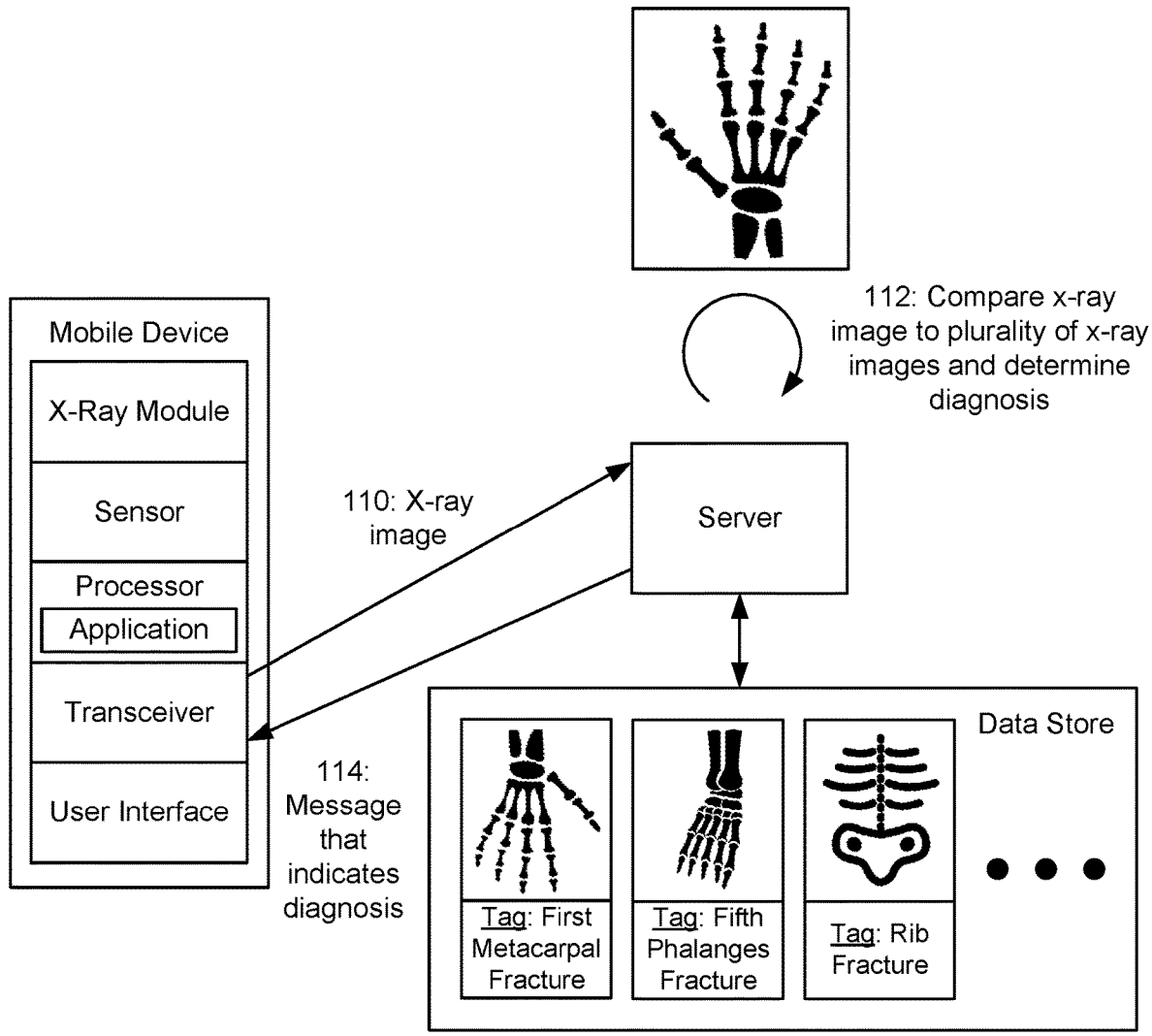
Figure 1C:
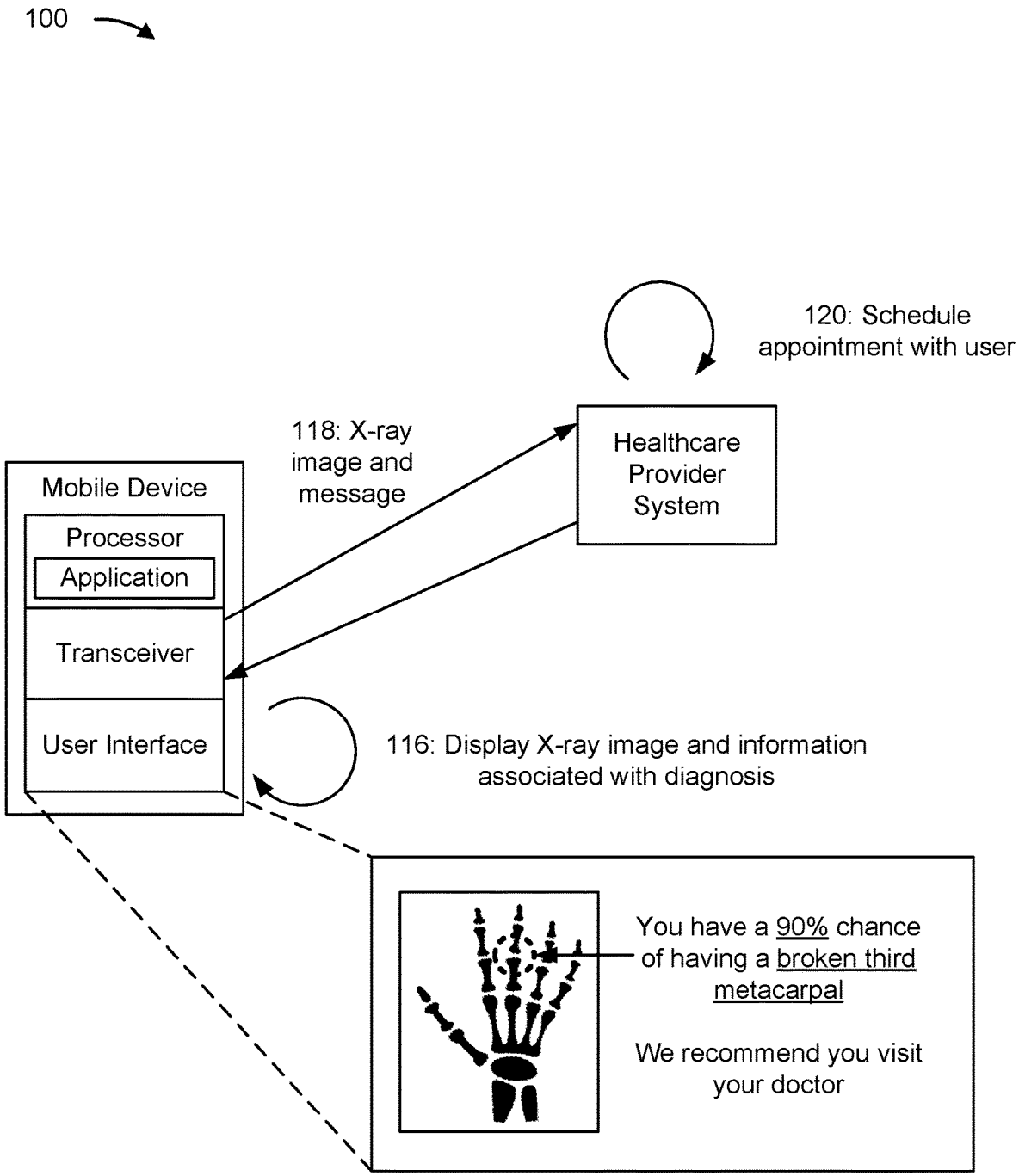

FIGS. 1A-1C are diagrams of an example 100 related to generating x-ray images and indicating diagnoses associated with the x-ray images. As shown in FIGS. 1A-1C, example 100 includes a mobile device, a server, and a healthcare provider system. These devices are described in more detail in connection with FIGS. 5 and 6.

In some implementations, the mobile device may include an x-ray module. The x-ray module may produce x-rays to be directed towards a body part. The x-ray module may have a form factor that allows the x-ray module to reside within the mobile device. The x-ray module may include polymers that produce the x-rays using triboluminescence or other applicable techniques (e.g., computerized tomography).

The x-ray module within the mobile device may be different than traditional x-ray components that would be unable to fit within the mobile device. The traditional x-ray components may include an anode, a cathode, an x-ray tube, and other components with size dimensions and/or weights that prevent them from being incorporated into the mobile device.

In some implementations, the mobile device may include a battery source that powers the x-ray module. The battery source may be a dedicated power source for the x-ray module (and not used for any other components of the mobile device), or the battery source may be a common power source used to power numerous components of the mobile device (e.g., the x-ray module and one or more other components). The battery source may be capable of providing a voltage that is sufficient to power the x-ray module, which may consume a relatively large amount of power as compared to other components of the mobile device. The battery source may be an aluminum-ion battery, a lithium-sulfur battery, or a graphene supercapacitor. The battery source may be sufficient to guarantee a certain number of x-ray instances and/or a certain number of x-ray images, before needing to be recharged.

In some implementations, the mobile device may include a sensor (e.g., a first sensor, such as an x-ray sensor) operable to detect electromagnetic radiation, such as x-rays. The sensor may detect x-rays reflected from the body part. The sensor may generate signals (e.g., first signals) based on the x-rays reflected from the body part. The sensor may be a complementary metal oxide semiconductor (CMOS) sensor, a charge-coupled device (CCD) sensor, a negative channel metal oxide semiconductor (NMOS) sensor, or another suitable type of sensor capable of detecting x-rays.

In some implementations, the mobile device may include a camera. The camera may provide an image of a view of a perspective of the mobile device. The image may include a target to be x-rayed, such as the body part.

In some implementations, the mobile device may include a user interface, such as a graphical user interface. The user interface may include controls for initiating an x-ray scan of the body part, stopping or pausing the x-ray scan of the body part, displaying x-ray images generated from the x-ray scan of the body part, and so on. The user interface may provide information and/or alerts associated with the x-ray scan of the body part.

As shown in FIG. 1A, and by reference number 102, the mobile device may receive, via the user interface, an instruction to initiate the x-ray scan. The mobile device may receive the instruction from a user of the mobile device via the user interface. For example, the user may select a "start" button via the user interface to initiate the x-ray scan, which may involve the x-ray module emitting the x-rays. In some implementations, the user interface may display a notification confirming whether to initiate the x-ray scan, in order to prevent the user from being accidentally exposed to x-ray radiation. In some implementations, the mobile device may receive the instruction to initiate the x-ray scan at an application that executes using a processor of the mobile device. The application may be responsible for facilitating x-ray scans performed at the mobile device.

In some implementations, the user may hold the mobile device in front of the body part to be x-rayed, such that the body part is visible to the x-ray module. The user interface may display instructions to guide the user to appropriately hold the mobile device in front of the body part to be x-rayed. Further, the user interface may display images generated by the camera, which may indicate the view from the perspective of the mobile device. The view may include the body part to be x-rayed. As a result, the user may easily view the body part to be x-rayed and position the mobile device appropriately to be in front of the body part.

Additionally, or alternatively, the mobile device may emit such instructions using audio (e.g., in case the body part is located at a position where the user cannot both see the user interface and point the x-ray module at the body part) to direct the user to properly position the mobile device. For example, the user may be x-raying their back, so the audio instructions may assist the user when pointing the mobile device at a specific area of their back to be x-rayed. The mobile device may determine, using computer vision and the images generated by the camera, whether the mobile device is pointed too close or too far away from the body part, or whether only a portion of the body part is visible to the x-ray module. Distances for whether the body part is too close or too far away may depend on a type of body part to be x-rayed, a capability of the x-ray module, and so on. The mobile device may generate audio instructions, based on the determination, which may guide the user to adjust a position or orientation of the mobile device so that the x-rays may be properly directed towards the body part.

As shown by reference number 104, the mobile device may emit, via the x-ray module, x-rays towards the body part. The mobile device may emit, via the x-ray module, the x-rays based on the instruction received via the user interface. Further, the mobile device may emit, via the x-ray module, the x-rays based on a confirmation to initiate the x-ray scan, which may be indicated via the user interface.

In some implementations, the mobile device may determine whether a first condition (e.g., an emission prevention condition) is satisfied, and the mobile device may refrain from emitting, via the x-ray module, the x-rays when the first condition satisfied. In some implementations, the mobile device may refrain from emitting the x-rays based on a determination that the user (e.g., via the mobile device or the x-ray module) is attempting to x-ray an invalid target. Additionally, or alternatively, the mobile device may refrain from emitting x-rays based on detecting the invalid target (e.g., in a path of x-rays that would be emitted from the x-ray module). In some implementations, the mobile device may refrain from emitting the x-rays based on a determination that an adjustment to a position of the body part is needed in order to accurately x-ray the body part. In some implementations, the mobile device may refrain from emitting the x-rays based on a determination that a level of radiation exposure, expected to be associated with the x-rays, exceeds a threshold. In these cases, the first condition may be satisfied based on the invalid target being detected, the adjustment needed to the position of the body part, and/or the level of radiation exposure exceeding the threshold.

Additional details related to determining the invalid target, determining that the adjustment to the position of the body part is needed, and determining the level of radiation exposure and performing actions based on the level of radiation exposure are described in connection with FIGS. 2 and 3.

In some implementations, the mobile device may display, via the user interface, one or more alerts when the first condition is satisfied. For example, an alert may be output (e.g., displayed on the user interface, emitted via a speaker of the mobile device, or the like) when the invalid target is detected. An alert may be output when the adjustment to the position of the body part to be x-rayed is needed. An alert may be output when the level of radiation exposure expected to be associated with the x-rays exceeds the threshold.

In some implementations, the mobile device may determine whether a second condition (e.g., an emission condition) is satisfied, and the mobile device may emit, via the x-ray module, the x-rays when the second condition is satisfied. The mobile device may emit the x-rays based on a determination that a user (e.g., via the mobile device and/or the x-ray module) is attempting to x-ray a valid target. Additionally, or alternatively, the mobile device may emit the x-rays based on detecting the valid target (e.g., in a path of x-rays to be emitted from the x-ray module). The mobile device may emit the x-rays based on a determination that the position of the body part in relation to the mobile device is suitable for x-raying the body part. The mobile device may emit the x-rays based on a determination that the level of radiation exposure expected to be associated with the x-rays does not exceed the threshold. In these cases, the second condition may be satisfied based on detecting the valid target, determining that no adjustment needed to the position of the body part, and/or determining that the level of radiation exposure does not exceed the threshold.

Additional details related to determining the valid target, determining that the adjustment to the position of the body part is not needed, and determining that the level of radiation exposure is acceptable are described in connection with FIGS. 2 and 3.

In some implementations, based on the one or more alerts that are output based on the first condition being satisfied, one or more actions may be performed in order to satisfy the second condition. For example, the user may move the mobile device to be directed towards the valid target. The user may move the mobile device, based on instructions output by the mobile device, such that the position of the body part in relation to the mobile device is suitable for x-raying the body part (e.g., the body part is in a path of x-rays to be emitted from the x-ray module). Additionally, or alternatively, the mobile device may adjust one or more properties of the x-rays (e.g., wavelength and/or duration of emission), and/or the user may move the body part to be x-rayed based on instructions displayed via the user interface, which may reduce the level of radiation exposure. As a result, the second condition may be satisfied (and/or the first condition may no longer be satisfied), and the mobile device may emit the x-rays.

As shown by reference number 106, the sensor may detect x-rays reflected from the body part. In other words, x-rays emitted from the x-ray module may hit the body part, and some of those x-rays may be reflected from the body part and detected by the sensor. The sensor may generate signals based on the x-rays detected from the body part.

In some implementations, the x-rays may be produced using triboluminescence, and the sensor may detect radiation that reflects from the body part. Backscatter x-ray is an advanced x-ray imaging technology that allows the radiation reflected from the body part to be detected by the sensor. Backscatter x-ray may be used in applications for which less destructive examination is desired, and may operate even if only one side of a target (e.g., one side of the body part) is available for examination. Backscatter x-ray may differ from traditional x-ray machines that detect hard and soft materials by variations in x-ray intensity transmitted through the target.

As shown by reference number 108, the application may generate an x-ray image of the body part using the signals. The processor may form the x-ray image using the signals, where the signals are electronic representations of the x-rays reflected from the body part.

As an example, the user of the mobile device may wish to x-ray their hand after sustaining an injury to the hand. The user may hold the mobile device in front of their hand. The application responsible for facilitating the x-ray scans may be opened on the mobile device. The user interface may display the image of the view from the perspective of the mobile device, and the user interface may display prompts that aid the user in holding their hand a certain distance from the mobile device. The user interface may display the notification to confirm whether the x-ray scan should be initiated, and the user interface may receive the confirmation to initiate the x-ray scan. The mobile device may emit, via the x-ray module, the x-rays towards the hand of the user based on one or more conditions being satisfied (e.g., valid target, correct position of hand in relation to the mobile device, and/or an acceptable level of radiation exposure). The mobile device may detect, via the sensor, x-rays reflected from the hand of the user and generate signals based on the reflected x-rays. The mobile device may generate, via the application, an x-ray image of the hand of the user.

As shown in FIG. 1B, and by reference number 110, the mobile device may transmit, via a transceiver of the mobile device, the x-ray image (e.g., data representative of the captured image) of the body part to a server. The server may process the x-ray image and determine a diagnosis associated with the x-ray image. In some implementations, the server may execute in a cloud computing system.

As shown by reference number 112, the server may compare the x-ray image of the body part to a plurality of x-ray images stored in a data store of the server. The plurality of x-ray images may include x-ray images from a plurality of patients, where each x-ray image associated with a patient may be tagged with a confirmed diagnosis. The server may compare the x-ray image of the body part to the plurality of x-ray images using image recognition and related techniques. The server may determine which x-ray image stored in the data store of the server is most similar to the x-ray image of the body part, as compared to other x-ray images of the plurality of images. After selecting the x-ray image that is most similar to the x-ray image of the body part, the server may determine the diagnosis associated with the x-ray image of the body part based on the confirmed diagnosis associated with the x-ray image selected from the plurality of x-ray images. In some cases, the diagnosis may indicate that no injury or problem is detected from the x-ray image.

In some implementations, the server may receive, from the mobile device, an indication of a type of body part associated with the x-ray image. The mobile device may receive, via the user interface, user input that indicates the type of body part associated with the x-ray image, which the mobile device may forward to the server along with the x-ray image. The server may compare the x-ray image of the body part to a subset of x-ray images in the plurality of x-ray images. The subset of x-ray images may correspond to the type of body part indicated by the mobile device. As a result, the server may reduce a quantity of x-ray images that are processed when determining the x-ray image stored in the data store that is most similar to the x-ray image of the body part.

In some implementations, the server may execute a machine learning model, which may be capable of determining diagnoses from x-ray images. The machine learning model may be trained using the plurality of x-ray images from the plurality of patients, where each x-ray image associated with the patient may be tagged with the confirmed diagnosis. The x-ray image of the body part may be input into the machine learning model, and the diagnosis associated with the x-ray image of the body part may be provided from the machine learning model as an output.

As an example, the plurality of x-ray images may be associated with a plurality of different problems, such as fractures, cancers, etc. The plurality of x-ray images may include different x-ray images for different fractures, such as first metacarpal fractures, fifth phalanges fractures, rib fractures, and so on. Further, even for a particular type of fracture (e.g., a first metacarpal fracture), the plurality of x-ray images may include multiple x-ray images that show different variations of first metacarpal fractures.

In some implementations, the diagnosis may be associated with a confidence score. The confidence score may indicate a likelihood that the diagnosis is correct. The confidence score may be based on a degree of similarity between the x-ray image of the body part, as received from the mobile device, and the x-ray image stored in the data store that is most similar to the x-ray image of the body part. The confidence score may be based on multiple degrees of similarity, each between the x-ray image of the body part, as received from the mobile device, and multiple x-ray images that are most similar to the x-ray image of the body part as compared to other x-ray images stored on the data store. The confidence score may be based on an output from the machine learning model. As an example, a confidence score may indicate a 90% likelihood that a diagnosis of a fractured toe is correct.

As shown by reference number 114, the mobile device may receive, via the transceiver and from the server, a message (e.g., a first message) that indicates the diagnosis. The message may indicate the confidence score associated with the diagnosis.

As shown in FIG. 1C, and by reference number 116, the mobile device may display, via the user interface, the x-ray image of the body part and information associated with the diagnosis. In some cases, the mobile device may display the diagnosis and the confidence score associated with the diagnosis (e.g., a diagnosis of a broken third metacarpal with a 90% likelihood). In some cases, the mobile device may display the diagnosis, which may indicate that no injury or problem is detected from the x-ray image. In some cases, the mobile device may only display a message for the user to visit a healthcare provider. In these cases, the diagnosis may be associated with a confidence score that does not satisfy a threshold (e.g., a confidence score of 50% or less), or the diagnosis may be particularly sensitive in nature (e.g., lung cancer) and should be relayed via the healthcare provider and not via the mobile device. In other words, the information associated with the diagnosis that is displayed may be based on the diagnosis itself.

As shown by reference number 118, the mobile device may transmit, via the transceiver, the x-ray image and the message indicating the diagnosis to a healthcare provider system associated with the healthcare provider. The mobile device may store contact information associated with the healthcare provider. As a result, if the user makes an appointment with the healthcare provider, the x-ray image and the diagnosis may already be accessible to the healthcare provider. In some implementations, the mobile device may display, via the user interface, a confirmation that the x-ray image and the diagnosis associated with the x-ray image has been provided to the healthcare provider.

As shown by reference number 120, the healthcare provider system may initiate a scheduling of an appointment with the user based on the x-ray image and the diagnosis.

The healthcare provider system may analyze the x-ray image and the diagnosis. The healthcare provider system may determine whether the appointment is recommended based on the x-ray image and the diagnosis. Depending on whether the appointment is recommended, the healthcare provider system may proactively initiate the scheduling of the appointment of the user.

As indicated above, FIGS. 1A-1C are provided as an example. Other examples may differ from what is described with regard to FIGS. 1A-1C. The number and arrangement of devices shown in FIGS. 1A-1C are provided as an example. In practice, there may be additional devices, fewer devices, different devices, or differently arranged devices than those shown in FIGS. 1A-1C. Furthermore, two or more devices shown in FIGS. 1A-1C may be implemented within a single device, or a single device shown in FIGS. 1A-1C may be implemented as multiple, distributed devices. Additionally, or alternatively, a set of devices (e.g., one or more devices) shown in FIGS. 1A-1C may perform one or more functions described as being performed by another set of devices shown in FIGS. 1A-1C. For example, operations described as being performed by the server may be performed by the mobile device, in some implementations.

Figure 2:
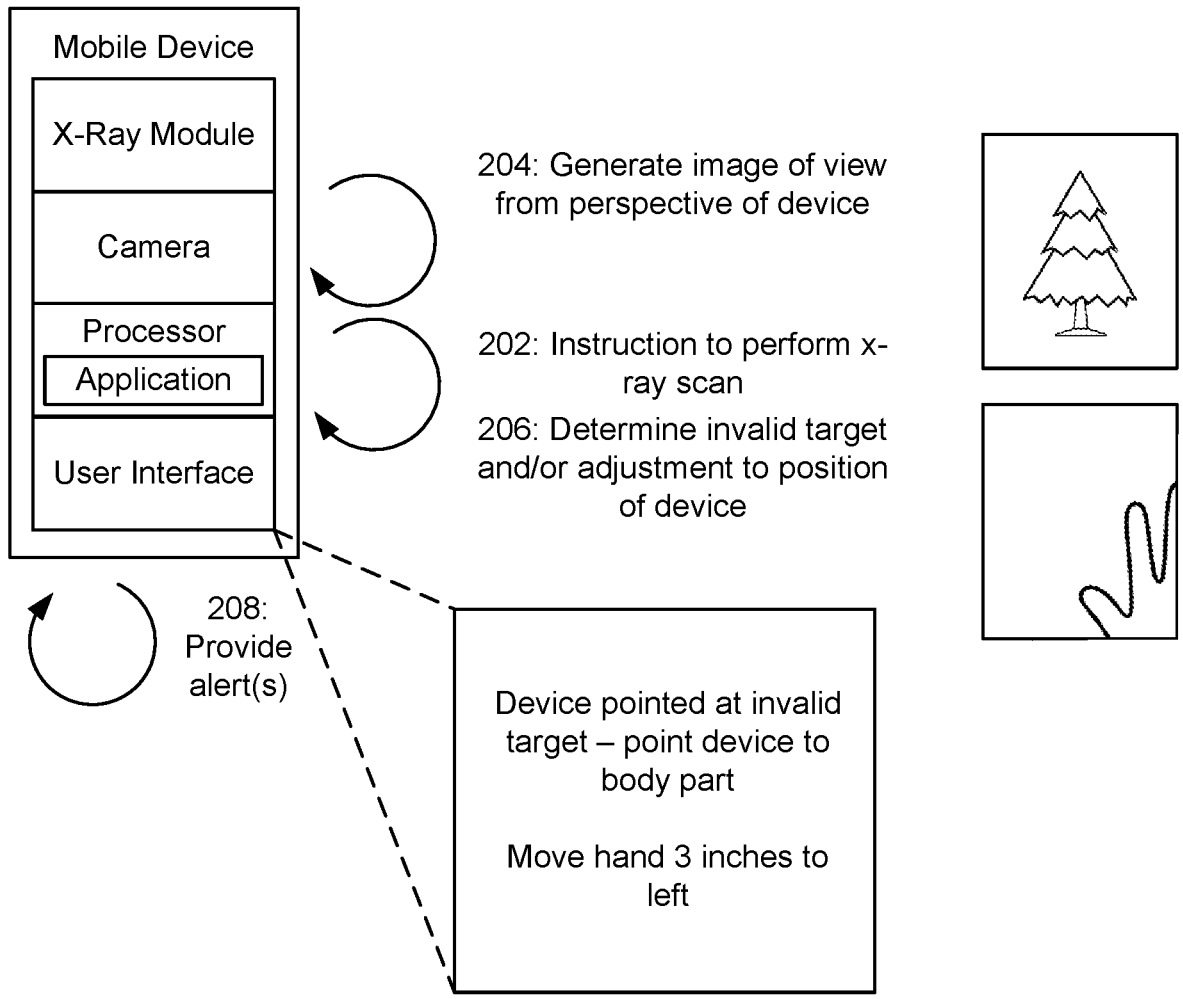
FIGS. 2-3 are diagrams of examples relating to providing alerts associated with x-rays.

FIG. 2 is a diagram of an example 200 related to providing alerts associated with x-rays. As shown in FIG. 2, example 200 includes a mobile device, which is described in more detail in connection with FIGS. 5 and 6.

As shown by reference number 202, the mobile device may receive, via a user interface of the mobile device, an instruction to initiate an x-ray scan. The mobile device may receive the instruction to initiate the x-ray scan at an application that executes on a processor of the mobile device. The application may be responsible for facilitating x-ray scans performed at the mobile device.

As shown by reference number 204, the mobile device may generate, using a camera of the mobile device, an image of a view from a perspective of the mobile device. The image may include a target to be x-rayed by the mobile device, where the target may be a valid target or an invalid target. A valid target may be a body part of a user to be x-rayed using the mobile device, whereas an invalid target may be a non-human object (e.g., a tree or a desk) or an area of the human body that is particularly sensitive, such as the brain, in which case the x-ray should be conducted by a healthcare provider.

As shown by reference number 206, the mobile device may determine, using the processor, whether the mobile device is pointed towards a valid target or an invalid target. The mobile device may determine from the image whether the mobile device is pointed towards the valid target or the invalid target. The mobile device may perform an image recognition, an object detection or object recognition, or a related technique for determining whether the target indicated in the image is valid or invalid. The mobile device may identify the target using the image recognition and compare an identifier associated with the target to a list of valid objects and/or a list of invalid objects. When the identifier associated with the target is included in the list of valid objects or in the list of invalid objects, the mobile device may determine that the target is valid or invalid, respectively.

In some implementations, the mobile device may emit low power radio waves, such as radar, to determine whether the mobile device is pointed towards the valid target or the invalid target. The mobile device may detect the radio waves reflected from the target, and depending on whether or not the reflected radio waves correspond to characteristics of skin, the mobile device may determine that the target is valid or invalid (e.g., valid if skin is detected, and invalid if skin is not detected). In some implementations, the mobile device may include a temperature sensor, which may be able to detect a temperature without physically touching the skin of the user. The mobile device may determine, via the temperature sensor, whether a detected temperature falls within a range or outside the range. The mobile device may determine whether the target is valid or invalid based on the detected temperature. For example, when the detected temperature is outside of a range associated with humans (e.g., outside of 95-100 degrees Fahrenheit), the mobile device may determine that the target is invalid (e.g., the target is a non-human object).

In some implementations, the mobile device may determine, using the processor, whether an adjustment to a position of the mobile device is needed to enable an x-ray module of the mobile device to direct x-rays towards the body part. The mobile device may use image recognition, object recognition, depth perception, and/or other related techniques to determine the position of the body part relative to the mobile device. The mobile device may determine whether the adjustment needs to be made based on objects and associated depths detected in the image. The mobile device may determine from the image whether the position of the mobile device is to be adjusted to enable the x-ray module of the mobile device to direct x-rays towards the body part. An adjustment to the position of the mobile device may involve moving the mobile device closer to the body part, moving the mobile device further away from the body part, or moving the mobile device to fully capture the body part.

For example, using image recognition or object recognition, the mobile device may determine that the target is only partially visible to the x-ray module, such that x-rays emitted from the x-ray module may not sufficiently strike the body part of the user. As another example, using image depth perception techniques or other related techniques, the mobile device may determine that the target is too far away or too close to the mobile device, such that x-rays emitted from the x-ray module may not result in an accurate x-ray image of the body part.

As shown by reference number 208, the mobile device may display, via the user interface, one or more alerts. The mobile device may display an alert indicating that the mobile device is pointed towards the invalid target. The mobile device may provide an alert indicating that the adjustment to the position of the mobile device is needed in order to perform an x-ray scan. The alert may include guidance in adjusting the position of the mobile device and/or the body part (e.g., move body part 5 inches closer to the mobile device), such that the mobile device may be able to perform the x-ray scan.

As an example, the user may point the mobile device at a tree and attempt to take an x-ray image of the tree. The mobile device may determine, using the camera, that the mobile device is pointed towards an invalid target. The mobile device may display, via the user interface, an alert indicating that the mobile device is pointed towards an invalid target and that the mobile device should instead be pointed towards a body part. As another example, the user may point the mobile device at the user's hand when attempting to take an x-ray image. The mobile device may determine, using the camera, that the user's hand is only partially visible to the x-ray module of the mobile device. The mobile device may display, via the user interface, an alert indicating that the user's hand should be moved 3 inches to the left so that x-ray image may be produced.

In some implementations, when the mobile device displays the one or more alerts relating to the invalid target and/or the position of the mobile device, a condition may be satisfied and the mobile device may not emit any x-rays via the x-ray module. However, when the condition is no longer satisfied or when another condition is satisfied (e.g., a valid target and/or a suitable position of the mobile device is met), the mobile device may emit x-rays via the x-ray module.

As indicated above, FIG. 2 is provided as an example. Other examples may differ from what is described with regard to FIG. 2.

Figure 3:
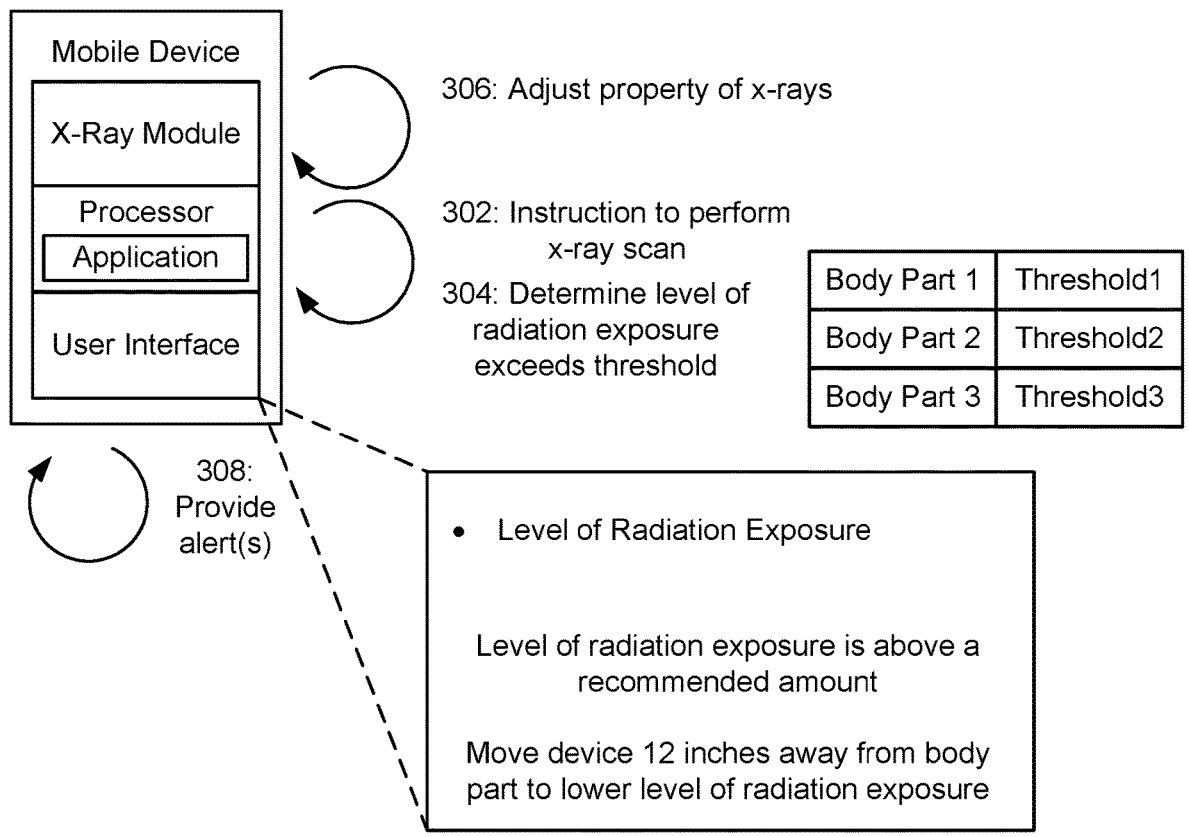

FIG. 3 is a diagram of an example 300 related to providing alerts associated with x-rays. As shown in FIG. 3, example 300 includes a mobile device, which is described in more detail in connection with FIGS. 5 and 6.

As shown by reference number 302, the mobile device may receive, via a user interface of the mobile device, an instruction to initiate an x-ray scan. The mobile device may receive the instruction to initiate the x-ray scan at an application that executes on a processor of the mobile device. The application may be responsible for facilitating x-ray scans performed at the mobile device. In some implementations, an x-ray module of the mobile device may emit x-rays towards a body part of a user based on the instruction to initiate the x-ray scan.

As shown by reference number 304, the mobile device may determine a level of radiation exposure associated with the x-rays. The level of radiation exposure may be a total amount of radiation exposure that is based on an amount of radiation exposure per a time period (e.g., an amount of radiation exposure per second) and a duration of radiation exposure. In some implementations, the mobile device may determine the level of radiation exposure prior to the x-rays being emitted. In this case, the level of radiation exposure may be a total expected amount of radiation exposure, which may be based on an expected level of radiation exposure per the time period and an expected duration associated with the x-rays. Additionally, or alternatively, the mobile device may determine the level of radiation exposure during an emission of the x-rays. In this case, the level of radiation exposure may be an actual level of radiation exposure, which may be based on an actual level of radiation exposure per the time period and an actual duration associated with the x-rays.

In some implementations, the mobile device may determine whether the level of radiation exposure (e.g., the total amount of radiation exposure and/or an amount of radiation exposure per a time period) satisfies (e.g., is greater than, or is greater than or equal to) a threshold. In some implementations, the threshold may be based on a type of body part that is being x-rayed. The threshold may be set based on acceptable levels of radiation exposure for certain types of x-ray imaging. For example, an x-ray scan of a first body part may be associated with a first threshold, an x-ray scan of a second body part may be associated with a second threshold, and so on. In some cases, the threshold may be based on characteristics of the user associated with the body part, such as gender, weight, age, and so on. In other words, the threshold may be custom based on the characteristics of the user and based on the type of body part that is being x-rayed. The characteristics and/or the type of body part being x-rayed may be input via the user interface. Additionally, or alternatively, the type of body part may be detected via image processing of an image of the body part captured by the camera of the mobile device.

In some implementations, a history of x-ray imaging performed by the mobile device may be stored on the mobile device, and subsequent x-ray imaging performed by the mobile device may be based on the history of x-ray imaging. The mobile device may limit, via the processor, an amount of radiation exposure associated with x-rays emitted by the x-ray module, where the limit may be based on the history of x-ray imaging. For example, a threshold associated with the amount of radiation exposure that is permitted may be set per hour, per day, etc. As an example, when the mobile device has already exceeded the threshold associated with the amount of radiation exposure, the mobile device may prevent the subsequent x-ray imaging until a later time (e.g., a next hour), or the subsequent x-ray imaging may need to be associated with a different user. In some cases, the threshold associated with the amount of radiation exposure may be on a per user basis.

As an example, a threshold for an x-ray scan of a lumbar spine may be 1.4 millisievert (mSv), a threshold for an x-ray scan of an extremity (e.g., hand or foot) may be 0.001 mSv, a threshold for an x-ray scan associated with a bone densitometry may be 0.001 mSv, a threshold for an x-ray scan associated with a mammography may be 0.21 mSv, a threshold for an x-ray scan associated with a three-dimensional mammogram may be 0.27 mSv, and so on.

As shown by reference number 306, a processor of the mobile device may instruct the x-ray module to adjust a property of the x-rays that are emitted towards the body part. The processor may instruct the x-ray module to adjust an intensity and/or duration of the x-rays that are emitted, which may cause the level of radiation exposure to be less than the threshold. In some implementations, the processor may instruct the x-ray module to stop emitting subsequent x-rays. In other words, the processor may prevent the subsequent x-rays from being emitted from the x-ray module. The processor may allow the subsequent x-rays after a certain period of time. In some implementations, the processor may determine a recommendation to reduce the level of radiation exposure. For example, the processor may determine that moving the mobile device further away from the body part or performing some other action may reduce the level of radiation exposure.

In some implementations, the mobile device may produce, via the x-ray module, the x-rays with a level of radiation exposure that is less than or equal to a threshold, where the threshold may depend on the type of body part that is being x-rayed. The level of radiation exposure may also be dependent on the type of body part that is being scanned. The x-ray module may be configured to not exceed a certain value (e.g., 0.1 mSv). However, in some cases, external factors, user error, and/or machine malfunctions may cause the level of radiation exposure associated with the emitted x-rays to be above the threshold or to be approaching the threshold. In these cases, the processor may perform one or more actions (e.g., adjust the property of the x-rays, stop emitting subsequent x-rays, provide the recommendation) to reduce the level of radiation exposure.

As shown by reference number 308, the mobile device may display, via the user interface, or may otherwise output one or more alerts associated with the level of radiation exposure. The mobile device may output an alert indicating that the level of radiation exposure is above a recommended amount. The mobile device may output an alert that x-rays emitted from the mobile device may be stopped or paused for a certain amount of time due to relatively high radiation exposure. The mobile device may output an alert with a recommendation to reduce the level of radiation exposure.

For example, the alert may indicate that the user should move their body part a distance of 12 inches further away from the mobile device to lower the level of radiation exposure.

In some implementations, the mobile device may display, via the user interface, or may otherwise output information associated with the level of radiation exposure corresponding to the x-rays emitted from the mobile device. For example, the mobile device may output an indication of the level of radiation exposure expected from x-raying the body part and/or a radiation exposure duration associated with x-raying the body part. In some implementations, the user interface may display a prompt requesting for the user to acknowledge the information associated with the level of radiation exposure corresponding to the x-rays emitted from the mobile device. After the user interface receives a selection that indicates acknowledgement from the user, the x-rays may be emitted from the mobile device.

In some implementations, when the mobile device displays the one or more alerts relating to the level of radiation exposure (e.g., the level of radiation exposure exceeds the threshold), a condition may be satisfied and the mobile device may not emit any x-rays via the x-ray module. However, when the condition is no longer satisfied or when another condition is satisfied (e.g., the level of radiation exposure is less than a threshold), the mobile device may emit x-rays via the x-ray module.

As indicated above, FIG. 3 is provided as an example. Other examples may differ from what is described with regard to FIG. 3.

Figure 4A:
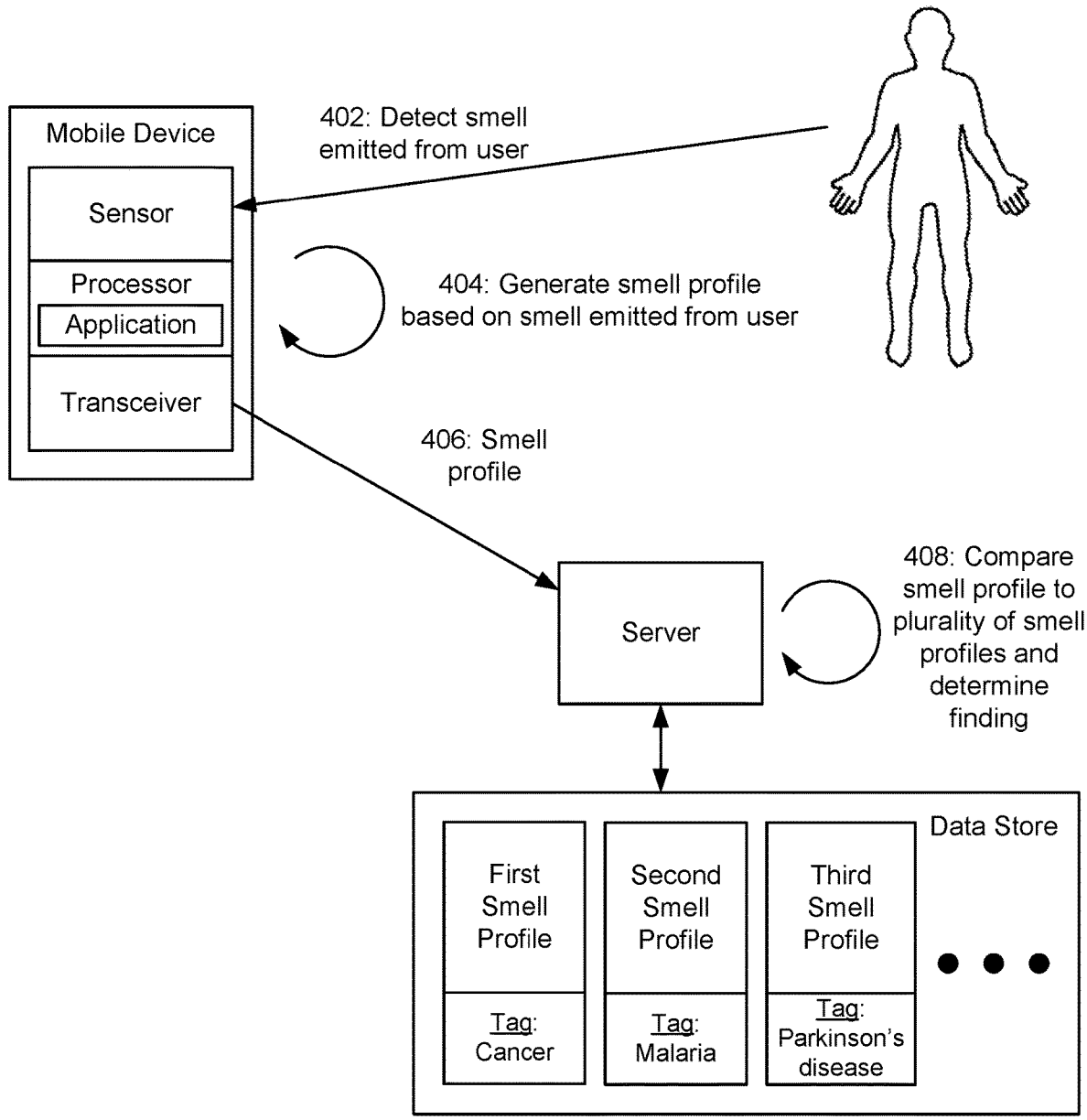
FIGS. 4A-4B are diagrams of an example relating to indicating findings associated with smells of users.
Figure 4B:
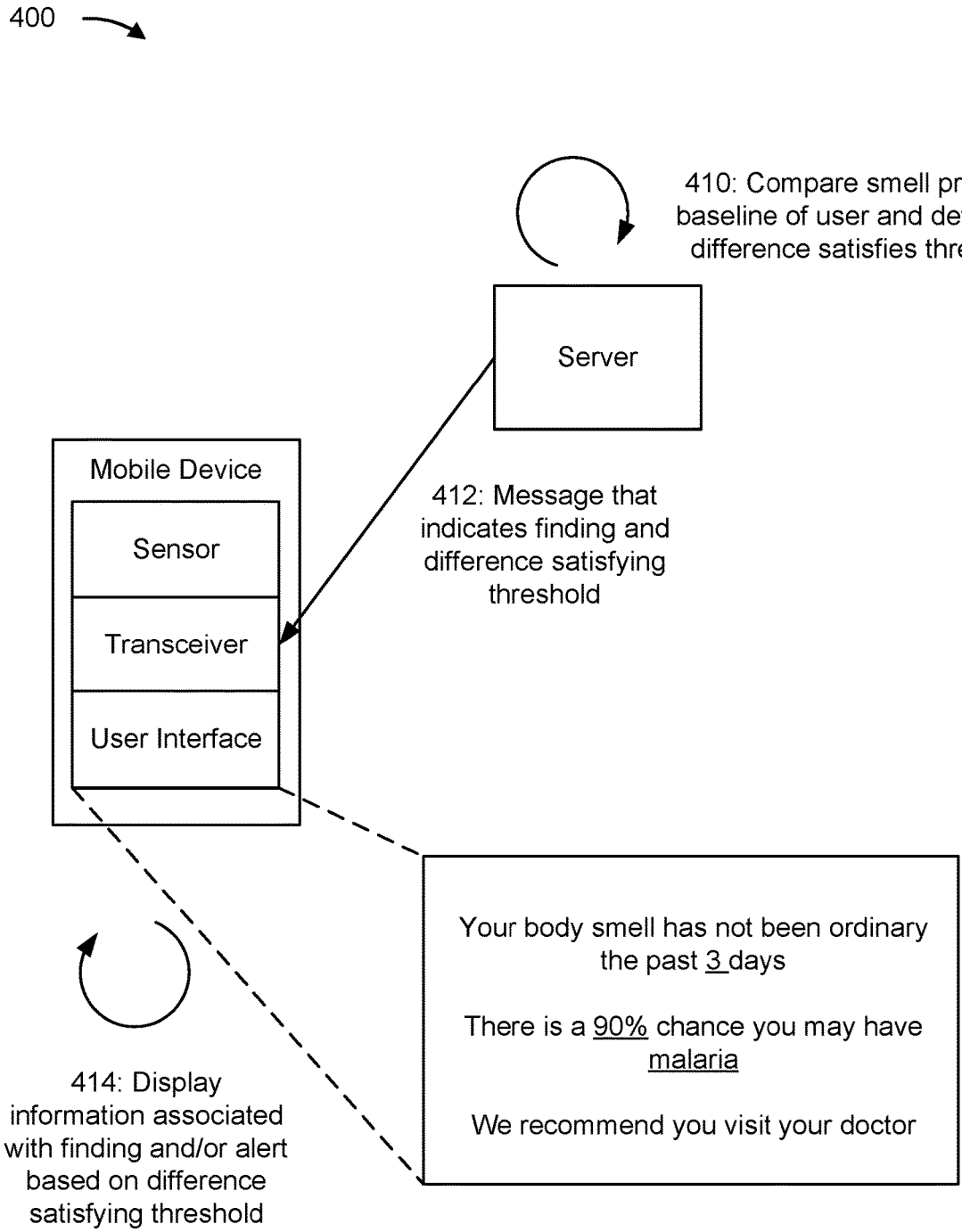

FIGS. 4A-4B are diagrams of an example 400 related to indicating findings associated with smells of users. As shown in FIGS. 4A-4B, example 400 includes a mobile device and a server. These devices are described in more detail in connection with FIGS. 5 and 6.

As shown in FIG. 4A, and by reference number 402, the mobile device may detect, via a sensor of the mobile device (e.g., a second sensor, such as a smell sensor or a chemical sensor), odor molecules emitted from a user associated with the mobile device. The odor molecules may be associated with a smell emitted from the user. The sensor may detect levels of chemicals emitted by the user, such as sulfur, ammonia, and/or volatile elements. The sensor may be a CMOS sensor, a CCD sensor, an NMOS sensor, or another suitable type of sensor capable of detecting smells emitted from the user. The sensor may detect the smells emitted from the user and generate signals (e.g., second signals) based on the smells emitted from the user.

In some implementations, the sensor may continually or periodically detect the smells emitted from the user over a period of time. Since the user is likely to carry the mobile device or often be in close proximity (e.g., less than 5 feet) from the mobile device, the sensor may continually or periodically detect the smells emitted from the user over the period of time. In some implementations, the sensor may detect the smells emitted from the user without input from the user or based on initial settings configured by the user.

In some implementations, the sensor may use electronic olfaction. Electronic olfaction may use nano sensors and/or sensor arrays to differentially detect certain volatile molecules (e.g., organic compounds). The sensor (or electronic nose) may act as a nose or receptor for odor molecules. Electronic olfaction may also involve using associated software to interpret information from the sensor based on a database of previously collected and analyzed odors. The sensor may utilize silicon photonics based sensor technologies.

As shown by reference number 404, the mobile device may generate, using an application that executes using a processor of the mobile device, a smell profile of the user based on the smells emitted from the user over the period of time. The smell profile may indicate values associated with different chemicals emitted by the user. For example, the smell profile may indicate a first value associated with a first chemical, a second value associated with a second chemical, and so on. The smell profile may be updated over time as the different chemicals emitted by the user and corresponding values change over time.

As shown by reference number 406, the mobile device may transmit, via a transceiver of the mobile device, the smell profile to a server. The server may be process the smell profile and determine a finding associated with the smell profile. In some implementations, the server may execute in a cloud computing system.

As shown by reference number 408, the server may compare the smell profile of the user to a plurality smell profiles stored in a data store of the server. The plurality of smell profiles may include smell profiles from a plurality of patients, where each smell profile associated with a patient may be tagged with a confirmed finding. The server may compare the smell profile of the user to the plurality of smell profiles. The server may determine which smell profile stored in the data store of the server is most similar to the smell profile of the user, as compared to other smell profiles of the plurality of smell profiles. For example, smells profiles may be similar to each other when differences in values between different chemicals satisfy one or more thresholds. After selecting the smell profile that is most similar to the smell profile of the user, the server may determine the finding associated with the smell profile of the user based on the confirmed finding associated with the smell profile selected from the plurality of smell profiles.

In some implementations, the server may execute a machine learning model, which may be capable of determining findings from smell profiles. The machine learning model may be trained using the plurality of smell profiles from the plurality of patients, where each smell profile associated with the patient may be tagged with the confirmed finding. The smell profile of the user may be input into the machine learning model, and the finding associated with the smell profile of the user may be provided from the machine learning model as an output.

As an example, the plurality of smell profiles may be associated with a plurality of different problems, such as cancer, malaria, Parkinson's disease, etc. The plurality of smell profiles may include different smell profiles for different problems, such as a first smell profile for cancer, a second smell profile for malaria, a third smell profile for Parkinson's disease, and so on. Further, even for a particular type of problem (e.g., cancer), the plurality of smell profiles may include multiple smell profiles that show different variations of the problem.

In some implementations, the finding may be associated with a confidence score. The confidence score may indicate a likelihood that the finding is correct. The confidence score may be based on a degree of similarity between the smell profile of the user and the smell profile stored in the data store that is most similar to the smell profile of the user. The confidence score may be based on multiple degrees of similarity, each between the smell profile of the user and multiple smell profiles stored on the data store that are most similar to the smell profile of the user. The confidence score may be based on an output from the machine learning model. As an example, a confidence score may indicate a 90% likelihood that a finding of malaria is correct.

As shown in FIG. 4B, and by reference number 410, the server may compare the smell profile of the user to a baseline smell profile of the user. The baseline smell profile may be created, for example, when the user configures the initial settings associated with the sensor and the baseline smell profile may be stored on the server. The baseline smell profile may indicate baseline values for the user with regards to a plurality of different chemicals. In some implementations, the server may determine that a difference between the smell profile of the user and the baseline smell profile of the user satisfies a threshold. For example, the difference may satisfy the threshold when differences in values between different chemicals between the smell profile of the user and the baseline smell profile of the user satisfy one or more thresholds (e.g., a first difference for a first chemical satisfies a first threshold, a second difference for a second chemical satisfies a second threshold, and so on).

As shown by reference number 412, the mobile device may receive, via the transceiver and from the server, a message (e.g., a second message) that indicates the finding. The message may indicate the confidence score associated with the finding. Further, the message may indicate whether a current smell of the user, based on the smell profile of the user, is different than the baseline smell profile for that user.

As shown by reference number 414, the mobile device may display, via a user interface, or may otherwise output information associated with the finding and/or an alert based on the difference between the smell profile of the user and the baseline smell profile of the user satisfying the threshold. In some cases, the mobile device may display the finding and the confidence score associated with the finding (e.g., a finding of malaria with a 90% likelihood), along with the alert (e.g., the user's body smell has not be ordinary for the past three days). In other cases, the mobile device may only display a recommendation for the user to visit a healthcare provider. In these cases, the diagnosis may be associated with a confidence score that does not satisfy a threshold (e.g., a confidence score of 50% or less), or the finding may be particularly sensitive in nature (e.g., Parkinson's disease) and should be relayed via the healthcare provider and not via the mobile device.

As indicated above, FIGS. 4A-4B are provided as an example. Other examples may differ from what is described with regard to FIGS. 4A-4B. The number and arrangement of devices shown in FIGS. 4A-4B are provided as an example. In practice, there may be additional devices, fewer devices, different devices, or differently arranged devices than those shown in FIGS. 4A-4B. Furthermore, two or more devices shown in FIGS. 4A-4B may be implemented within a single device, or a single device shown in FIGS. 4A-4B may be implemented as multiple, distributed devices. Additionally, or alternatively, a set of devices (e.g., one or more devices) shown in FIGS. 4A-4B may perform one or more functions described as being performed by another set of devices shown in FIGS. 4A-4B. For example, operations described as being performed by the server may be performed by the mobile device, in some implementations.

Figure 5:
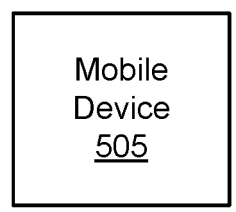
FIG. 5 is a diagram of an example environment in which systems and/or methods described herein may be implemented.
Figure 5:
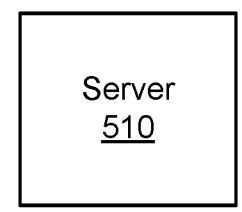
Figure 5:
Figure 5:
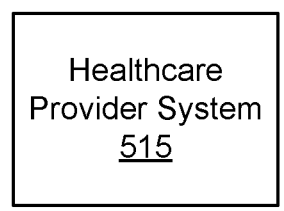

FIG. 5 is a diagram of an example environment 500 in which systems and/or methods described herein may be implemented. As shown in FIG. 5, environment 500 may include a mobile device 505, a server 510, a healthcare provider system 515, and a network 520. Devices of environment 500 may interconnect via wired connections, wireless connections, or a combination of wired and wireless connections.

The mobile device 505 includes one or more devices capable of receiving, generating, storing, processing, and/or providing information associated with generating x-ray images and/or smell profiles and indicating diagnoses and/or findings associated with the x-ray images and/or smell profiles, as described elsewhere herein. The mobile device 505 may include a communication device and/or a computing device. For example, the mobile device 505 may include a wireless communication device, a phone such as a smart phone, a mobile phone or a video phone, a user equipment, or a similar type of device. As described above, the mobile device 505 may include an x-ray module, a battery source, a sensor, a camera, a processor, a transceiver, a smell sensor, and/or a user interface.

The server 510 includes one or more devices capable of receiving, generating, storing, processing, providing, and/or routing information associated with generating x-ray images and/or smell profiles and indicating diagnoses and/or findings associated with the x-ray images and/or smell profiles, as described elsewhere herein. The server 510 may include a communication device and/or a computing device. For example, the server 510 may include a server, such as an application server, a client server, a web server, a database server, a host server, a proxy server, a virtual server (e.g., executing on computing hardware), or a server in a cloud computing system. In some implementations, the server 510 includes computing hardware used in a cloud computing environment.

The healthcare provider system 515 includes one or more devices capable of receiving, generating, storing, processing, providing, and/or routing information associated with x-ray images and/or smell profiles, as described elsewhere herein. The healthcare provider system 515 may include a communication device and/or a computing device. For example, the healthcare provider system 515 may include a server, such as an application server, a client server, a web server, a database server, a host server, a proxy server, a virtual server (e.g., executing on computing hardware), or a server in a cloud computing system. Additionally, or alternatively, the healthcare provider system 515 may include a phone (e.g., as a smart phone, a mobile phone or a video phone), a user equipment, a laptop computer, a tablet computer, a desktop computer, or a similar type of device. In some implementations, the healthcare provider system 515 includes computing hardware used in a cloud computing environment.

The network 520 includes one or more wired and/or wireless networks. For example, the network 520 may include a cellular network, a public land mobile network, a local area network, a wide area network, a metropolitan area network, a telephone network, a private network, the Internet, and/or a combination of these or other types of networks. The network 520 enables communication among the devices of environment 500.

The number and arrangement of devices and networks shown in FIG. 5 are provided as an example. In practice, there may be additional devices and/or networks, fewer devices and/or networks, different devices and/or networks, or differently arranged devices and/or networks than those shown in FIG. 5. Furthermore, two or more devices shown in FIG. 5 may be implemented within a single device, or a single device shown in FIG. 5 may be implemented as multiple, distributed devices. Additionally, or alternatively, a set of devices (e.g., one or more devices) of environment 500 may perform one or more functions described as being performed by another set of devices of environment 500.

Figure 6:
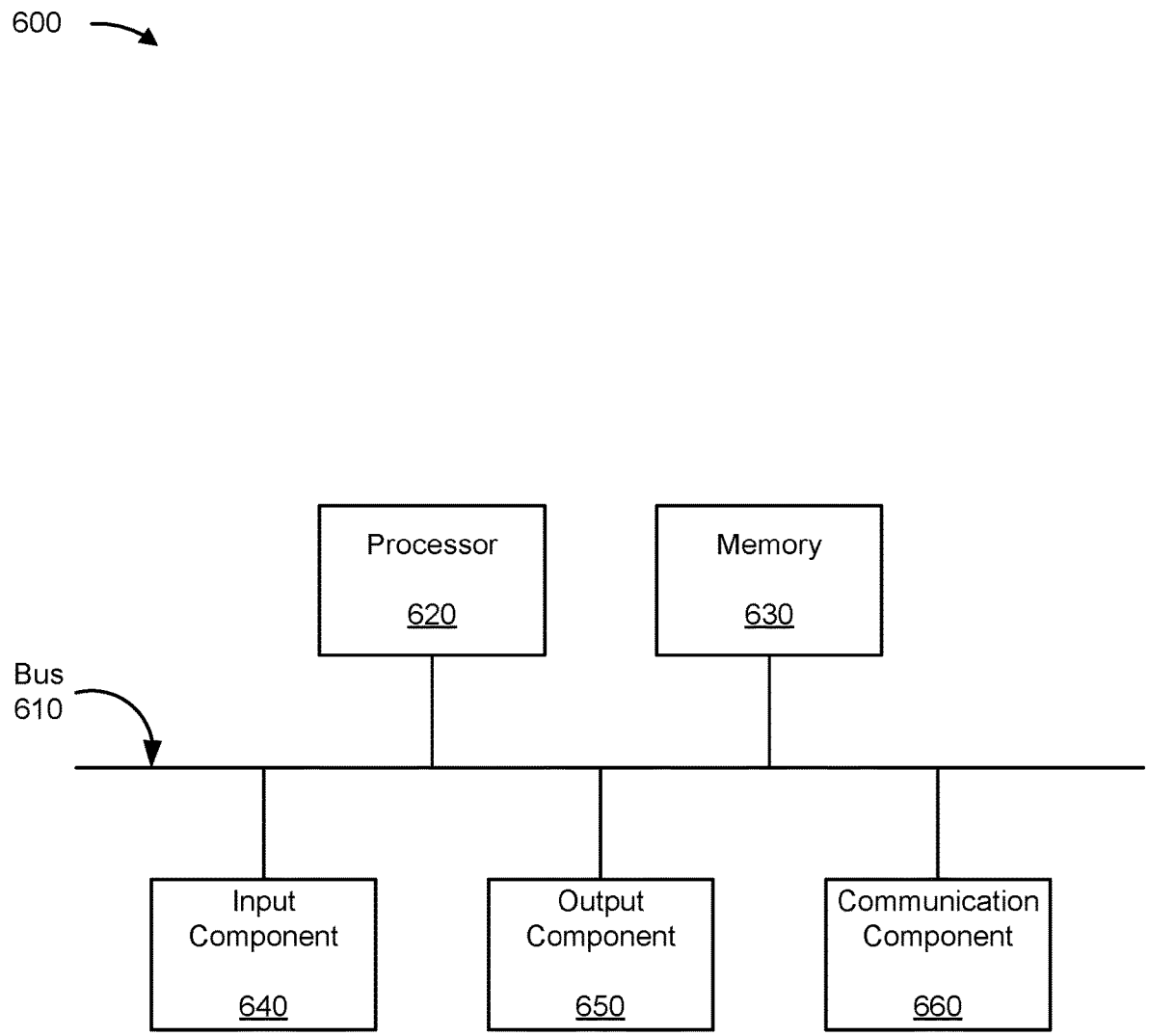
FIG. 6 is a diagram of example components of one or more devices of FIG. 5.

FIG. 6 is a diagram of example components of a device 600, which may correspond to mobile device 505, server 510, and/or healthcare provider system 515. In some implementations, mobile device 505, server 510, and/or healthcare provider system 515 include one or more devices 600 and/or one or more components of device 600. As shown in FIG. 6, device 600 may include a bus 610, a processor 620, a memory 630, an input component 640, an output component 650, and a communication component 660.

Bus 610 includes one or more components that enable wired and/or wireless communication among the components of device 600. Bus 610 may couple together two or more components of FIG. 6, such as via operative coupling, communicative coupling, electronic coupling, and/or electric coupling. Processor 620 includes a central processing unit, a graphics processing unit, a microprocessor, a controller, a microcontroller, a digital signal processor, a field-programmable gate array, an application-specific integrated circuit, and/or another type of processing component. Processor 620 is implemented in hardware, firmware, or a combination of hardware and software. In some implementations, processor 620 includes one or more processors capable of being programmed to perform one or more operations or processes described elsewhere herein.

Memory 630 includes volatile and/or nonvolatile memory. For example, memory 630 may include random access memory (RAM), read only memory (ROM), a hard disk drive, and/or another type of memory (e.g., a flash memory, a magnetic memory, and/or an optical memory). Memory 630 may include internal memory (e.g., RAM, ROM, or a hard disk drive) and/or removable memory (e.g., removable via a universal serial bus connection). Memory 630 may be a non-transitory computer-readable medium. Memory 630 stores information, instructions, and/or software (e.g., one or more software applications) related to the operation of device 600. In some implementations, memory 630 includes one or more memories that are coupled to one or more processors (e.g., processor 620), such as via bus 610.

Input component 640 enables device 600 to receive input, such as user input and/or sensed input. For example, input component 640 may include a touch screen, a keyboard, a keypad, a mouse, a button, a microphone, a switch, a sensor, a global positioning system sensor, an accelerometer, a gyroscope, and/or an actuator. Output component 650 enables device 600 to provide output, such as via a display, a speaker, and/or a light-emitting diode. Communication component 660 enables device 600 to communicate with other devices via a wired connection and/or a wireless connection. For example, communication component 660 may include a receiver, a transmitter, a transceiver, a modem, a network interface card, and/or an antenna.

Device 600 may perform one or more operations or processes described herein. For example, a non-transitory computer-readable medium (e.g., memory 630) may store a set of instructions (e.g., one or more instructions or code) for execution by processor 620. Processor 620 may execute the set of instructions to perform one or more operations or processes described herein. In some implementations, execution of the set of instructions, by one or more processors 620, causes the one or more processors 620 and/or the device 600 to perform one or more operations or processes described herein. In some implementations, hardwired circuitry is used instead of or in combination with the instructions to perform one or more operations or processes described herein. Additionally, or alternatively, processor 620 may be configured to perform one or more operations or processes described herein. Thus, implementations described herein are not limited to any specific combination of hardware circuitry and software.

The number and arrangement of components shown in FIG. 6 are provided as an example. Device 600 may include additional components, fewer components, different components, or differently arranged components than those shown in FIG. 6. Additionally, or alternatively, a set of components (e.g., one or more components) of device 600 may perform one or more functions described as being performed by another set of components of device 600.

Figure 7:
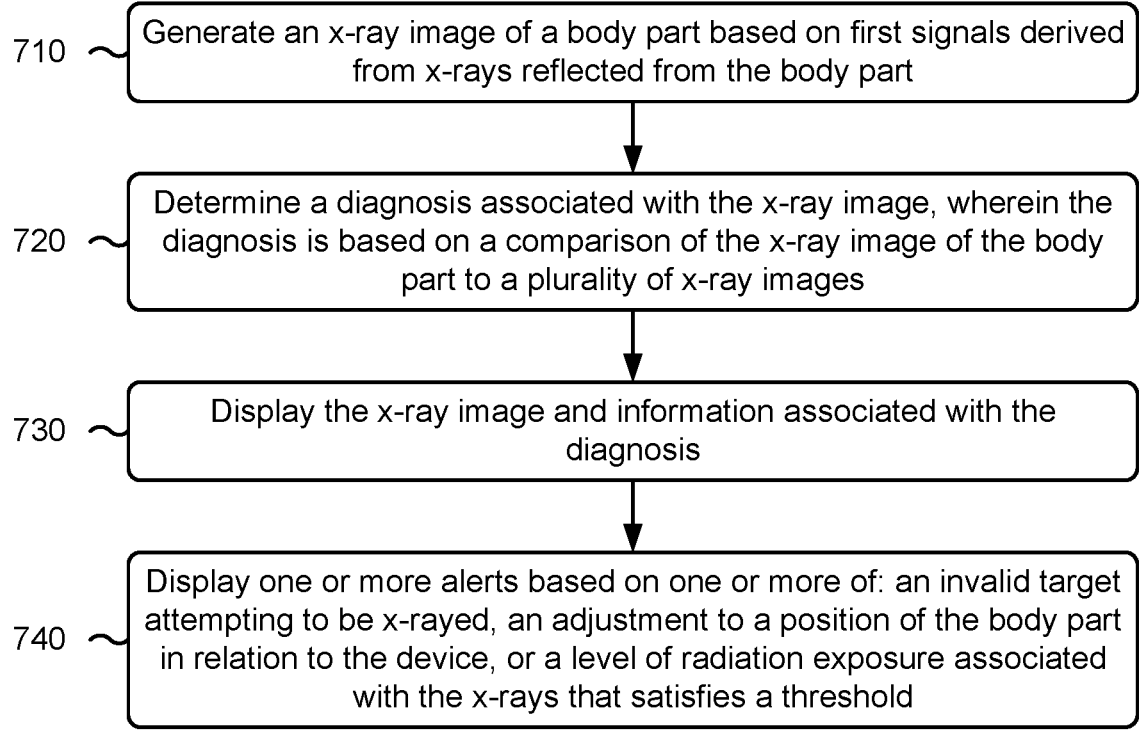
FIGS. 7-8 are flowcharts of example processes relating to generating x-ray images and indicating diagnoses associated with the x-ray images.

FIG. 7 is a flowchart of an example process 700 associated with generating x-ray images and indicating diagnoses associated with the x-ray images. In some implementations, one or more process blocks of FIG. 7 may be performed by a mobile device (e.g., mobile device 505). In some implementations, one or more process blocks of FIG. 7 may be performed by another device or a group of devices separate from or including the mobile device, such as server 510 and/or healthcare provider system 515. Additionally, or alternatively, one or more process blocks of FIG. 7 may be performed by one or more components of device 600, such as processor 620, memory 630, input component 640, output component 650, and/or communication component 660.

As shown in FIG. 7, process 700 may include generating an x-ray image of a body part based on first signals derived from x-rays reflected from the body part (block 710). As further shown in FIG. 7, process 700 may include determining a diagnosis associated with the x-ray image, wherein the diagnosis is based on a comparison of the x-ray image of the body part to a plurality of x-ray images (block 720). As shown in FIG. 7, process 700 may include displaying the x-ray image and information associated with the diagnosis (block 730). As further shown in FIG. 7, process 700 may include displaying one or more alerts based on one or more of: an invalid target attempting to be x-rayed, an adjustment to a position of the body part in relation to the device, or a level of radiation exposure associated with the x-rays that satisfies a threshold (block 740).

Although FIG. 7 shows example blocks of process 700, in some implementations, process 700 may include additional blocks, fewer blocks, different blocks, or differently arranged blocks than those depicted in FIG. 7. Additionally, or alternatively, two or more of the blocks of process 700 may be performed in parallel.

Figure 8:
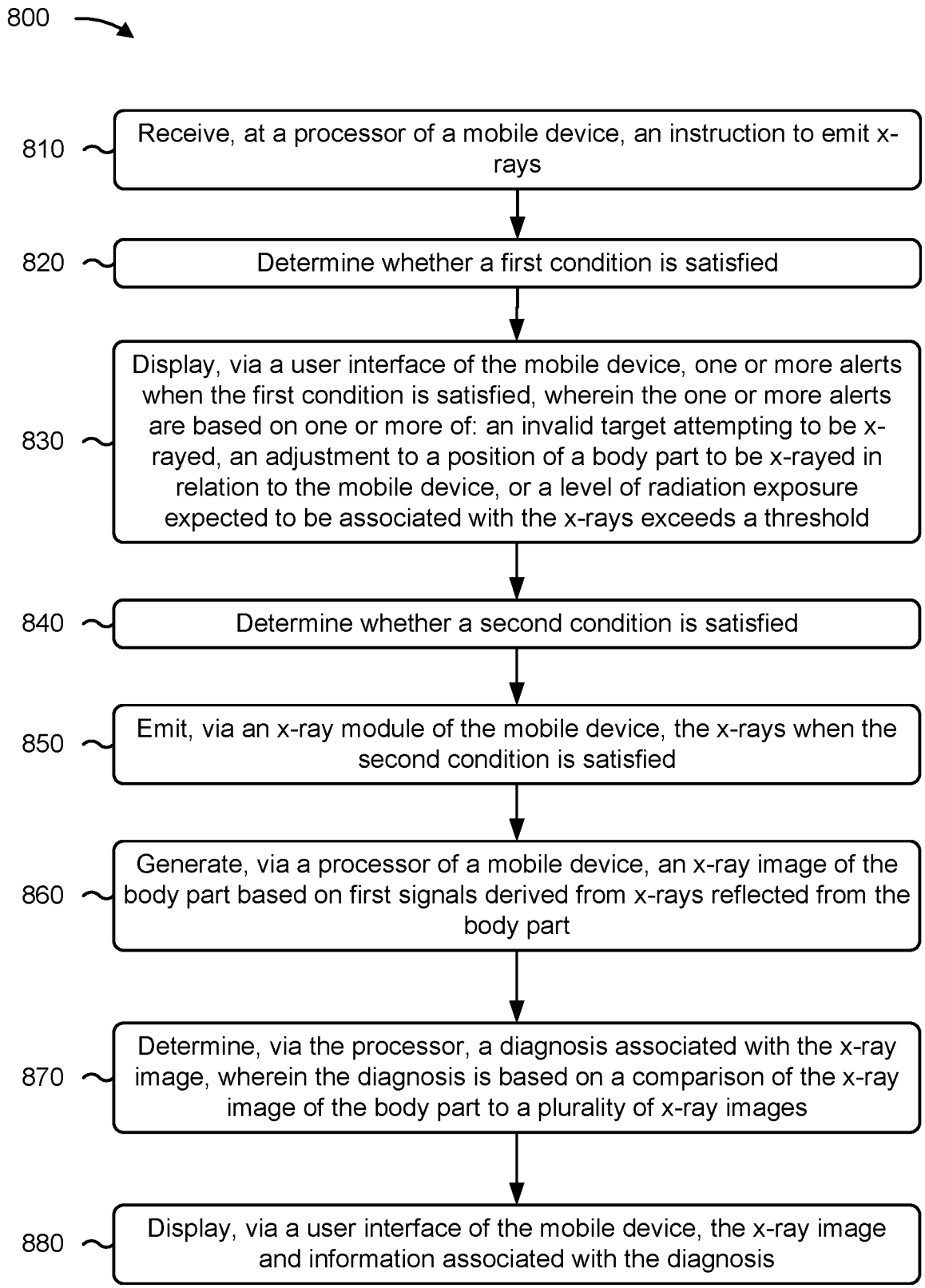

FIG. 8 is a flowchart of an example process 800 associated with generating x-ray images and indicating diagnoses associated with the x-ray images. In some implementations, one or more process blocks of FIG. 8 may be performed by a mobile device (e.g., mobile device 505). In some implementations, one or more process blocks of FIG. 8 may be performed by another device or a group of devices separate from or including the mobile device, such as server 510, and/or healthcare provider system 515. Additionally, or alternatively, one or more process blocks of FIG. 8 may be performed by one or more components of device 600, such as processor 620, memory 630, input component 640, output component 650, and/or communication component 660.

As shown in FIG. 8, process 800 may include receiving, at a processor of a mobile device, an instruction to emit x-rays (block 810). As further shown in FIG. 8, process 800 may include determining whether a first condition is satisfied (block 820). As further shown in FIG. 8, process 800 may include displaying, via a user interface of the mobile device, one or more alerts when the first condition is satisfied, wherein the one or more alerts are based on one or more of: an invalid target attempting to be x-rayed, an adjustment to a position of a body part to be x-rayed in relation to the mobile device, or a level of radiation exposure expected to be associated with the x-rays exceeds a threshold (block 830). As further shown in FIG. 8, process 800 may include determining whether a second condition is satisfied (block 840). As further shown in FIG. 8, process 800 may include emitting, via an x-ray module of the mobile device, the x-rays when the second condition is satisfied (block 850). As further shown in FIG. 8, process 800 may include generating, via a processor of a mobile device, an x-ray image of the body part based on first signals derived from x-rays reflected from the body part (block 860). As further shown in FIG. 8, process 800 may include determining, via the processor, a diagnosis associated with the x-ray image, wherein the diagnosis is based on a comparison of the x-ray image of the body part to a plurality of x-ray images (block 870). As further shown in FIG. 8, process 800 may include displaying, via a user interface of the mobile device, the x-ray image and information associated with the diagnosis (block 880).

Although FIG. 8 shows example blocks of process 800, in some implementations, process 800 may include additional blocks, fewer blocks, different blocks, or differently arranged blocks than those depicted in FIG. 8. Additionally, or alternatively, two or more of the blocks of process 800 may be performed in parallel.

In some implementations, a device includes an x-ray module operable to produce x-rays to be directed towards a body part; a first sensor operable to detect the x-rays reflected from the body part and generate first signals based on the x-rays reflected from the body part; a battery source that powers the x-ray module; and a processor configured to: generate an x-ray image of the body part using the first signals; transmit the x-ray image to a server; receive, from the server, a first message that indicates a diagnosis associated with the x-ray image, wherein the diagnosis is based on a comparison of the x-ray image of the body part to a plurality of x-ray images stored at the server; and provide, to a user interface of the device for display, the x-ray image and information that indicates the diagnosis associated with the x-ray image.

In some implementations, a device includes a memory; a processor, coupled to the memory, configured to: generate an x-ray image of a body part based on first signals derived from x-rays reflected from the body part; and determine a diagnosis associated with the x-ray image, wherein the diagnosis is based on a comparison of the x-ray image of the body part to a plurality of x-ray images; and a user interface configured to: display the x-ray image and a message that indicates the diagnosis associated with the x-ray image; and display one or more alerts based on one or more of: an invalid target attempting to be x-rayed, an adjustment to a position of the body part in relation to the device, or a level of radiation exposure associated with the x-rays that satisfies a threshold.

In some implementations, a method includes producing, via an x-ray module of a mobile device, x-rays to be directed towards a body part; detecting, via a first sensor of the mobile device, the x-rays reflected from the body part; generating, via the first sensor, first signals based on the x-rays reflected from the body part; generating, via a processor of the mobile device, an x-ray image of the body part based on the first signals; transmitting, via a transceiver of the mobile device, the x-ray image to a server; receiving, via the transceiver and from the server, a first message that indicates a diagnosis associated with the x-ray image, wherein the diagnosis is based on a comparison of the x-ray image of the body part to a plurality of x-ray images stored at the server; and displaying, via a user interface of the mobile device, the x-ray image and information associated with the diagnosis associated with the x-ray image.

In some implementations, a method includes receiving, at a processor of a mobile device, an instruction to emit x-rays; determining whether a first condition is satisfied; displaying, via a user interface of the mobile device, one or more alerts when the first condition is satisfied, wherein the one or more alerts are based on one or more of: an invalid target attempting to be x-rayed, an adjustment to a position of a body part to be x-rayed in relation to the mobile device, or a level of radiation exposure expected to be associated with the x-rays exceeds a threshold; determining whether a second condition is satisfied; emitting, via an x-ray module of the mobile device, the x-rays when the second condition is satisfied; generating, via a processor of a mobile device, an x-ray image of the body part based on first signals derived from x-rays reflected from the body part; determining, via the processor, a diagnosis associated with the x-ray image, wherein the diagnosis is based on a comparison of the x-ray image of the body part to a plurality of x-ray images; and displaying, via a user interface of the mobile device, the x-ray image and information associated with the diagnosis.

The foregoing disclosure provides illustration and description but is not intended to be exhaustive or to limit the implementations to the precise forms disclosed. Modifications and variations may be made in light of the above disclosure or may be acquired from practice of the implementations.

As used herein, the terms "substantially" and "approximately" mean "within reasonable tolerances of manufacturing and measurement." As used herein, "satisfying a threshold" may, depending on the context, refer to a value being greater than the threshold, greater than or equal to the threshold, less than the threshold, less than or equal to the threshold, equal to the threshold, not equal to the threshold, or the like.

Even though particular combinations of features are recited in the claims and/or disclosed in the specification, these combinations are not intended to limit the disclosure of various implementations. Many of these features may be combined in ways not specifically recited in the claims and/or disclosed in the specification. The disclosure of various implementations includes each dependent claim in combination with every other claim in the claim set. As used herein, a phrase referring to "at least one of" a list of items refers to any combination of those items, including single members. As an example, "at least one of: a, b, or c" is intended to cover a, b, c, a+b, a+c, b+c, and a+b+c, as well as any combination with multiples of the same element (e.g., a+a, a+a+a, a+a+b, a+a+c, a+b+b, a+c+c, b+b, b+b+b, b+b+c, c+c, and c+c+c, or any other ordering of a, b, and c).

No element, act, or instruction used herein should be construed as critical or essential unless explicitly described as such. Also, as used herein, the articles "a" and "an" are intended to include one or more items and may be used interchangeably with "one or more." Further, as used herein, the article "the" is intended to include one or more items referenced in connection with the article "the" and may be used interchangeably with "the one or more." Where only one item is intended, the phrase "only one," "single," or similar language is used. Also, as used herein, the terms "has," "have," "having," or the like are intended to be open-ended terms that do not limit an element that they modify (e.g., an element "having" A may also have B). Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A device, comprising:
an x-ray module operable to produce x-rays to be directed towards a body part;
a first sensor operable to detect the x-rays reflected from the body part and generate first signals based on the x-rays reflected from the body part;
a battery source operable to power the x-ray module; and
a processor configured to:
generate an x-ray image of the body part using the first signals;
transmit the x-ray image to a server;
receive, from the server, a first message providing a diagnosis of:
an injury or problem detected based on the x-ray image, or
no injury or problem is detected based on the x-ray image,
wherein the diagnosis is based on a comparison of the x-ray image of the body part to a plurality of x-ray images stored at the server; and
provide, to a user interface of the device for display, the x-ray image and text that indicates the diagnosis.

2. The device of claim 1, wherein the processor is further configured to:
transmit, to a system associated with a healthcare provider, the x-ray image and the first message providing the diagnosis.

3. The device of claim 1, further comprising:
a second sensor operable to detect odor molecules emitted from a user associated with the device and generate second signals based on the odor molecules emitted from the user; and
wherein the processor is further configured to:
generate a profile of the user using the second signals;
transmit the profile of the user to the server;
receive, from the server, a second message that indicates a finding associated with the profile of the user, wherein the finding is based on a comparison of the profile of the user to a plurality of profiles stored at the server; and
provide, to the user interface for display, information that indicates the finding associated with the profile of the user.

4. The device of claim 3, wherein the processor is further configured to:
compare the profile to a baseline profile of the user;
determine that a difference between the profile and the baseline profile satisfies a threshold; and
provide, to the user interface for display, an alert that indicates an odor emitted from the user is not ordinary based on the difference satisfying the threshold and a recommendation to consult with a healthcare provider.

5. The device of claim 1, wherein the processor is further configured to:
generate, using a camera of the device, an image of a view from a perspective of the device;
determine, from the image, that the x-ray module is pointed towards an invalid target; and
provide, to the user interface for display, an alert indicating that the x-ray module is pointed towards the invalid target.

6. The device of claim 1, wherein the processor is further configured to:
generate, using a camera of the device, an image of a view from a perspective of the device, wherein the image includes the body part to be x-rayed;
determine, from the image, an adjustment to a position of the device to enable the x-ray module to direct x-rays towards the body part, wherein the adjustment involves moving the device closer to the body part, moving the device further away from the body part, or moving the device to fully capture the body part; and
provide, to the user interface for display, an alert indicating the adjustment to the position of the device.

7. The device of claim 1, wherein the x-ray module is operable to produce the x-rays with a level of radiation exposure that is less than or equal to a threshold.

8. The device of claim 1, wherein the processor is further configured to:
determine a level of radiation exposure associated with the x-rays;
determine that the level of radiation exposure satisfies a threshold; and
adjust a property of the x-rays such that the level of radiation exposure is changed or prevent subsequent x-rays from being emitted from the x-ray module.

9. The device of claim 1, wherein the processor is further configured to:
determine a level of radiation exposure associated with the x-rays;
determine that the level of radiation exposure satisfies a threshold; and
provide, to the user interface for display, an alert indicating that the level of radiation exposure satisfies the threshold and a recommendation to reduce the level of radiation exposure.

10. The device of claim 1, wherein the processor is further configured to:
receive, via the user interface, a selection to capture the x-ray image of the body part;
provide, to the user interface for display, a notification confirming whether to generate the x-ray image of the body part;
receive, via the user interface, a confirmation to generate the x-ray image of the body part; and
instruct the x-ray module to produce the x-rays.

11. A device, comprising:
a memory;
a processor, coupled to the memory, configured to:
generate an x-ray image of a body part based on first signals derived from x-rays reflected from the body part; and
determine a diagnosis of:
an injury or problem detected based on the x-ray image, or
no injury or problem is detected based on the x-ray image,
wherein the diagnosis is based on a comparison of the x-ray image of the body part to a plurality of x-ray images; and
a user interface configured to:
display the x-ray image and text that indicates the diagnosis; and
display one or more alerts based on one or more of: an invalid target for the x-ray image, an adjustment to a position of the body part in relation to the device, or a level of radiation exposure associated with the x-rays that satisfies a first threshold.

12. The device of claim 11, wherein the user interface is further configured to:
- display, using a camera of the device, a view of a perspective of the device, wherein the view includes the body part to be x-rayed; or
- display a confirmation that the x-ray image and the diagnosis has been provided to a healthcare provider of a user associated with the device.

13. The device of claim 11, wherein the user interface is further configured to:
- display an indication of the level of radiation exposure expected from x-raying the body part, wherein the level of radiation exposure is a total amount of radiation exposure based on an amount of radiation exposure per a time period and a radiation exposure duration.

14. The device of claim 11, further comprising:
- an x-ray module operable to produce x-rays to be directed towards the body part, wherein the x-rays reflected from the body part are based on the x-rays directed towards the body part;
- a first sensor operable to detect the x-rays reflected from the body part and generate the first signals based on the x-rays reflected from the body part;
- a second sensor operable to detect odor molecules emitted from a user associated with the device and generate second signals based on the odor molecules emitted from the user; and
- a battery source operable to power the x-ray module.

15. The device of claim 11, wherein:
the processor is further configured to:
- generate a profile of a user associated with the device using second signals that are based on an odor emitted from the user;
- determine a finding associated with the profile of the user, wherein the finding is based on a comparison of the profile of the user to a plurality of profiles; and
- the user interface is further configured to display information that indicates the finding associated with the profile of the user.

16. The device of claim 15, wherein:
the processor is further configured to:
- compare the profile to a baseline profile of the user; and
- determine that a difference between the profile and the baseline profile satisfies a second threshold; and
the user interface is further configured to display an alert that indicates an odor emitted from the user is not ordinary based on the difference satisfying the second threshold and a recommendation to consult with a healthcare provider.

17. The device of claim 11, wherein:
the processor is further configured to:
- generate, using a camera of the device, an image of a view from a perspective of the device; and
- determine, from the image, that an x-ray module is pointed towards the invalid target; and
the user interface is further configured to display an alert indicating that the x-ray module is pointed towards the invalid target.

18. The device of claim 11, wherein:
the processor is further configured to:
- generate, using a camera of the device, an image of a view from a perspective of the device, wherein the image includes the body part to be x-rayed; and
- determine, from the image, the adjustment to the position of the device to enable an x-ray module to direct x-rays towards the body part, wherein the adjustment involves moving the device closer to the body part, moving the device further away from the body part, or moving the device to fully capture the body part; and
the user interface is further configured to display an alert indicating the adjustment to the position of the device.

19. The device of claim 11, wherein:
the processor is further configured to:
- determine the level of radiation exposure associated with the x-rays; and
- determine that the level of radiation exposure satisfies the first threshold; and
the user interface is further configured to display an alert indicating that the level of radiation exposure satisfies the first threshold and a recommendation to reduce the level of radiation exposure.

20. A method, comprising:
- producing, via an x-ray module of a mobile device, x-rays to be directed towards a body part;
- detecting, via a first sensor of the mobile device, the x-rays reflected from the body part;
- generating, via the first sensor, first signals based on the x-rays reflected from the body part;
- generating, via a processor of the mobile device, an x-ray image of the body part based on the first signals;
- transmitting, via a transceiver of the mobile device, the x-ray image to a server;
- receiving, via the transceiver and from the server, a first message providing a diagnosis of:
  - an injury or problem detected based on the x-ray image, or
  - no injury or problem is detected based on the x-ray image,
- wherein the diagnosis is based on a comparison of the x-ray image of the body part to a plurality of x-ray images stored at the server; and
- displaying, via a user interface of the mobile device, the x-ray image and text indicating the diagnosis.

21. The method of claim 20, further comprising:
- detecting, via a second sensor of the mobile device, odor molecules emitted from a user associated with the mobile device;
- generating, via the second sensor, second signals based on the odor molecules emitted from the user;
- generating, via the processor, a profile of the user based on the second signals;
- transmitting, via the transceiver, the profile of the user to the server;
- receiving, via the transceiver and from the server, a second message that indicates a finding associated with the profile of the user, wherein the finding is based on a comparison of the profile of the user to a plurality of profiles stored at the server; and
- displaying, via the user interface, information associated with the finding associated with the profile of the user.

22. A method, comprising:
- receiving, at a processor of a mobile device, an instruction to emit x-rays;
- determining whether a first condition is satisfied;
- displaying, via a user interface of the mobile device, one or more alerts when the first condition is satisfied, wherein the one or more alerts are based on one or more of: an invalid target attempting to be x-rayed, an adjustment to a position of a body part to be x-rayed in relation to the mobile device, or a level of radiation exposure expected to be associated with the x-rays exceeding a threshold;
- determining whether a second condition is satisfied;

emitting, via an x-ray module of the mobile device, the x-rays when the second condition is satisfied;

generating, via the processor of the mobile device, an x-ray image of the body part based on first signals derived from x-rays reflected from the body part;

determining, via the processor, a diagnosis of:
- an injury or problem detected based on the x-ray image, or
- no injury or problem is detected based on the x-ray image, wherein the diagnosis is based on a comparison of the x-ray image of the body part to a plurality of x-ray images; and displaying, via the user interface of the mobile device, the x-ray image and text indicating the diagnosis.

23. The method of claim 22, wherein the first condition is satisfied based on at least one of: a determination that the invalid target is attempting to be x-rayed, a determination to request the adjustment to the position of the body part to be x-rayed in relation to the mobile device, or a determination that the level of radiation exposure expected to be associated with the x-rays exceeds the threshold.

24. The method of claim 22, wherein the second condition is satisfied based on at least one of: a determination of a valid target attempting to be x-rayed, a determination that the position of the body part is suitable for x-raying the body part, or a determination that the level of radiation exposure expected to be associated with the x-rays does not exceed the threshold.

25. The device of claim 1, wherein:
the first message indicates a confidence score associated with the diagnosis, and
the text indicates the confidence score associated with the diagnosis.

* * * * *